United States Patent
Katayama

(10) Patent No.: US 10,844,420 B2
(45) Date of Patent: Nov. 24, 2020

(54) METHOD FOR DETECTING SLOW-VISA

(71) Applicant: JUNTENDO EDUCATIONAL FOUNDATION, Bunkyo-ku (JP)

(72) Inventor: Yuki Katayama, Bunkyo-ku (JP)

(73) Assignee: JUNTENDO EDUCATIONAL FOUNDATION, Bunkyo-ku (JP)

( * ) Notice: Subject to any disclaimer, the term of this patent is extended or adjusted under 35 U.S.C. 154(b) by 182 days.

(21) Appl. No.: 16/083,185

(22) PCT Filed: Mar. 7, 2017

(86) PCT No.: PCT/JP2017/008975
§ 371 (c)(1),
(2) Date: Sep. 7, 2018

(87) PCT Pub. No.: WO2017/154897
PCT Pub. Date: Sep. 14, 2017

(65) Prior Publication Data
US 2019/0093145 A1    Mar. 28, 2019

(30) Foreign Application Priority Data
Mar. 10, 2016 (JP) ................................ 2016-046496

(51) Int. Cl.
*C12Q 1/14* (2006.01)
(52) U.S. Cl.
CPC ..................... *C12Q 1/14* (2013.01)

(58) Field of Classification Search
CPC ...................................................... C12Q 1/14
See application file for complete search history.

(56) References Cited

PUBLICATIONS

Watanabe et al., J of Hospital Infection, 2001, 47:294-300.*
English translation of the International Search Report dated May 9, 2017 in PCT/JP2017/008975, 2 pages.
Yoshifumi Aiba, et al., "Mutation of RNA Polymerase β-Subunit Gene Promotes Heterogeneous-to-Homogeneous Conversion of β-Lactam Resistance in Methicillin-Resistant *Staphylococcus aureus*" Antimicrobial Agents Chemotherapy, vol. 57, No. 10, Oct. 2013, pp. 4861-4871.
Michie Saito, et al, "'Slow VISA,' a Novel Phenotype of Vancomycin Resistance, Found in Vitro in Heterogeneous Vancomycin-Intermediate *Staphylococcus aureus* Strain Mu3" Antimicrobial Agents Chemotherapy, vol. 58, No. 9, Sep. 2014, pp. 5024-5035.
Vicente Aguadero, et al, "An Analysis of the Association Between Genotype and Antimicrobial Resistance in Methicillin-Resistant *Staphylococcus aureus* Clinical Isolates" Rev. Esp. Quimioter., vol. 28, No. 2, 2015, pp. 79-85.
Keiichi Hiramatsu, et al. "Dissemination in Japanese Hospitals of Strains of *Staphylococcus aureus* Heterogeneously Resistant to Vancomycin" The Lancet, vol. 350, Dec. 6, 1997, pp. 1670-1673.

* cited by examiner

*Primary Examiner* — Bin Shen
(74) *Attorney, Agent, or Firm* — Oblon, McClelland, Maier & Neustadt, L.L.P.

(57) ABSTRACT

Described herein is a method for detecting slow-VISA from clinical samples.

19 Claims, 3 Drawing Sheets

[Figure 1]
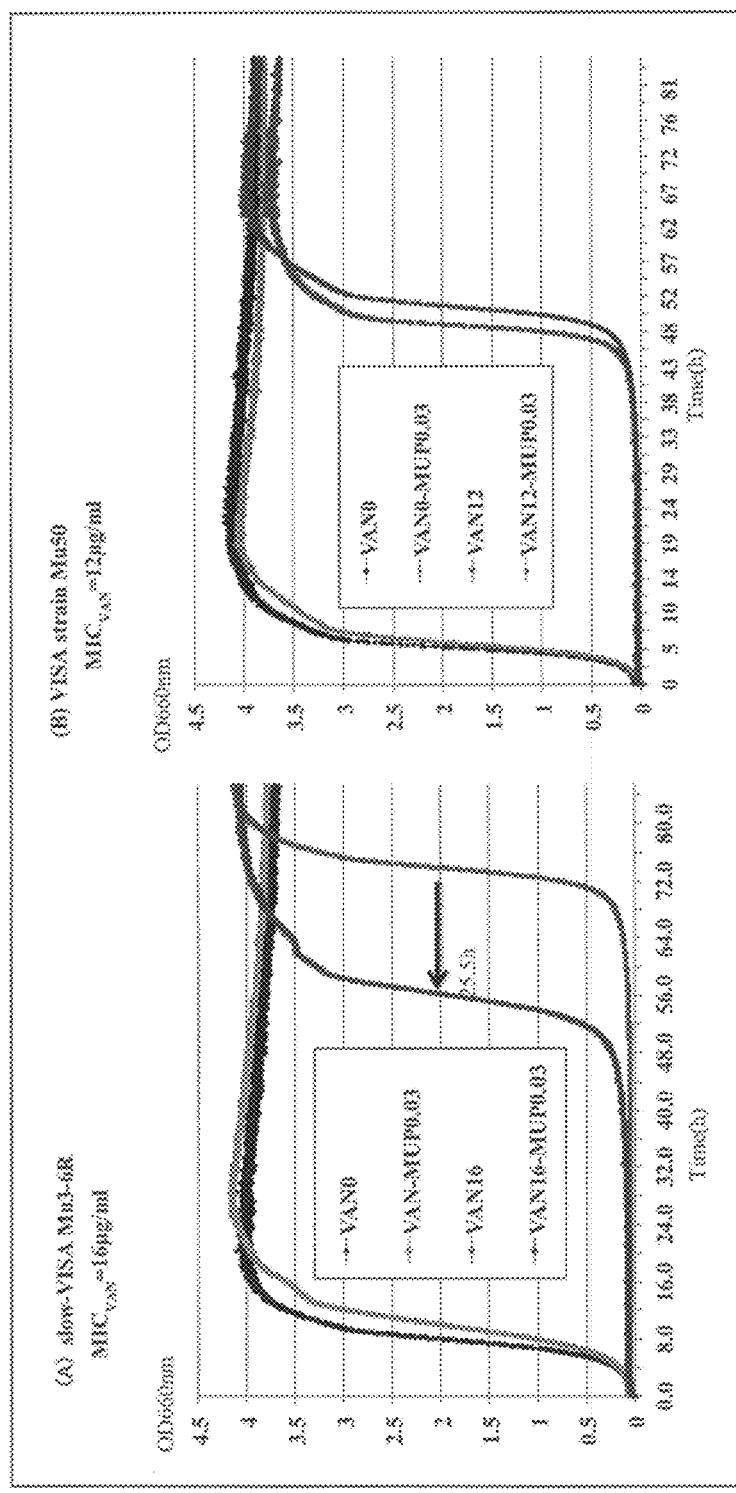

[Figure 2]
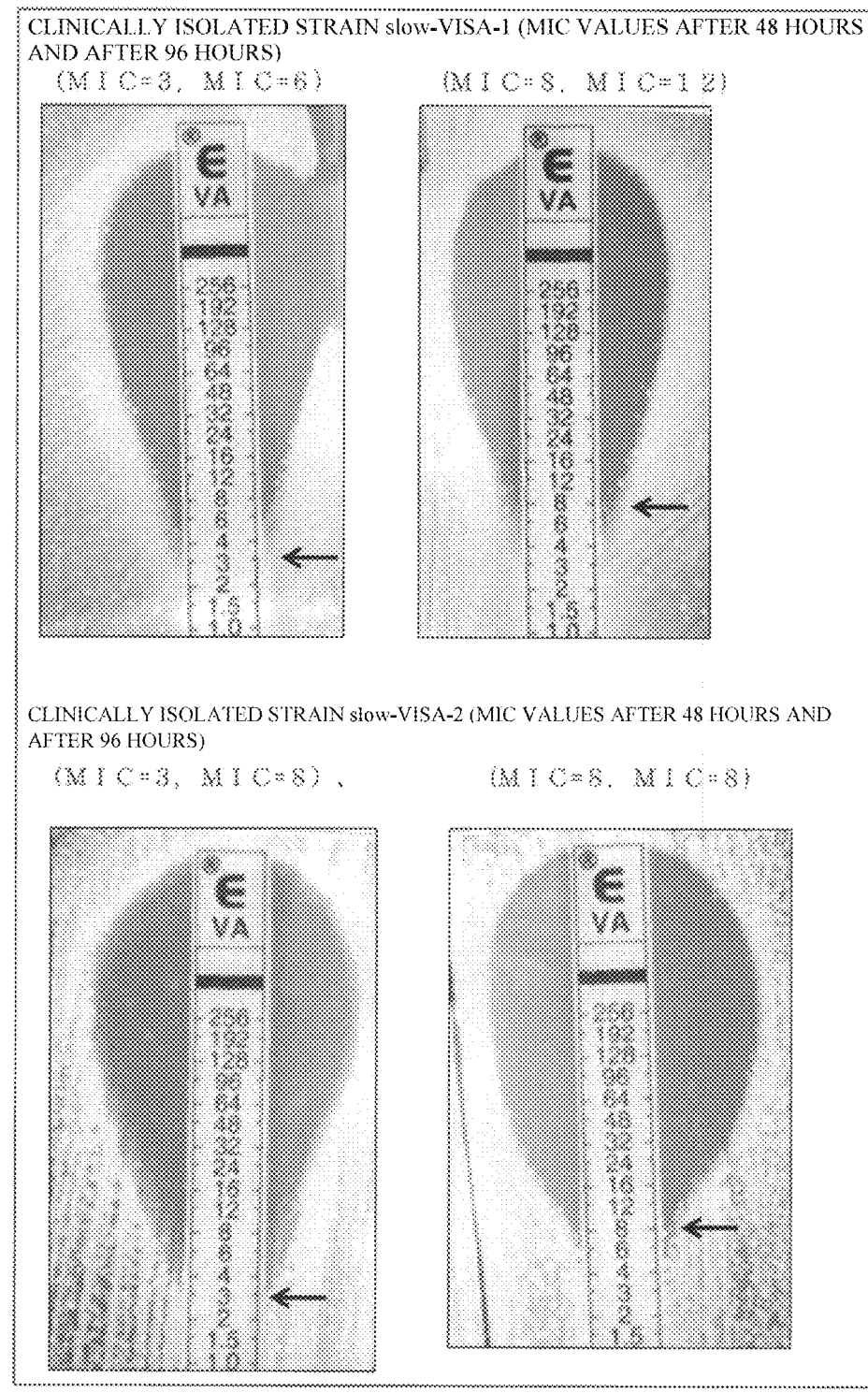

[Figure 3]
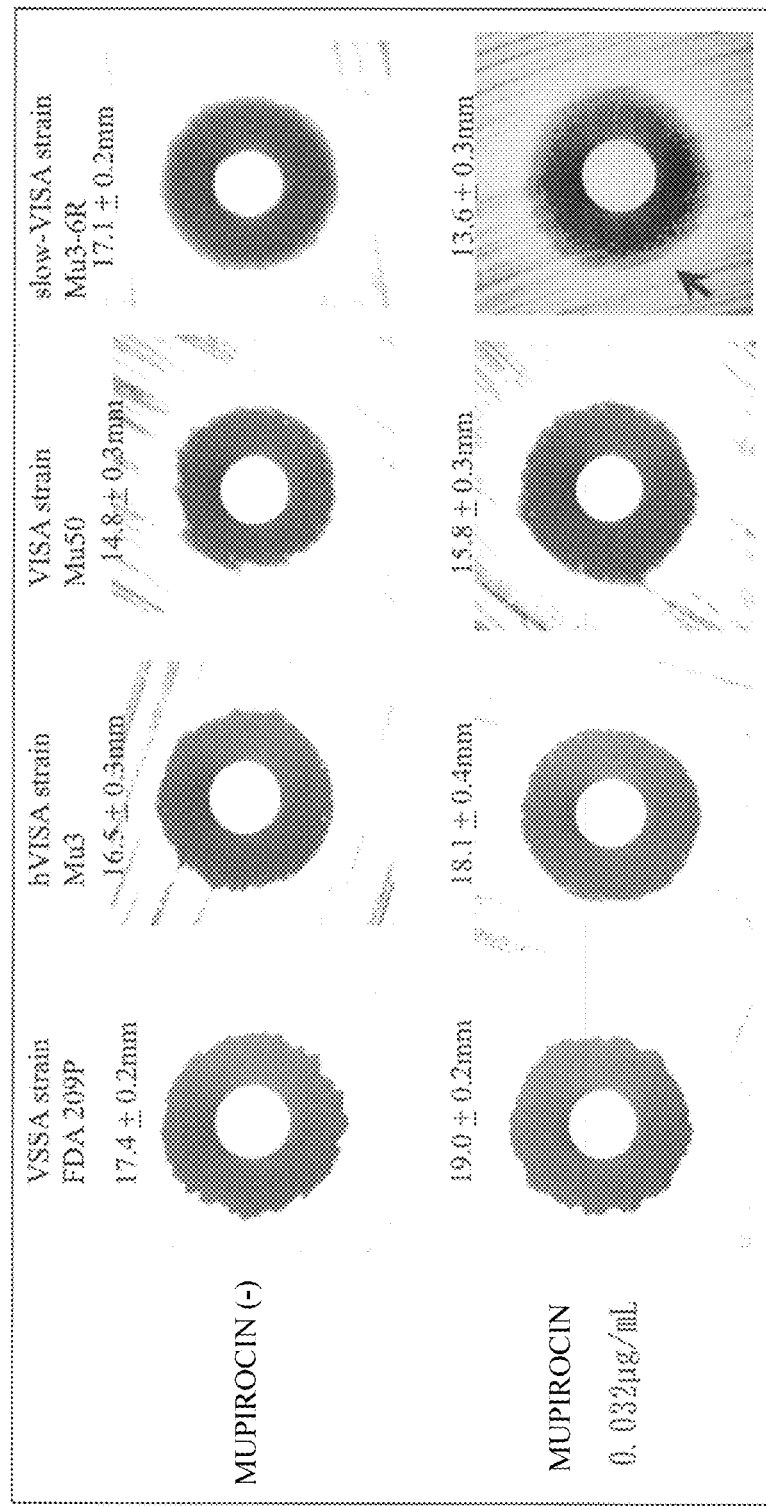

METHOD FOR DETECTING SLOW-VISA

FIELD OF THE INVENTION

The present invention relates to a method for detecting slow-VISA among vancomycin (VCM)-resistant bacteria against which VCM, which is an anti-methicillin-resistant *Staphylococcus aureus* (MRSA) agent, is not effective.

BACKGROUND OF THE INVENTION

Although the effect of antibiotics on bacterial infection is confirmed, the appearance of drug resistant bacteria has become a problem. In particular, MRSA is a bacterium that causes hospital infection, and thus it has become a social problem. Meanwhile, VCM was developed as the first-line drug for treatment of MRSA, and it was thought that the problem of resistant bacteria would be solved.

However, VCM-resistant enterococci (VRE), VCM intermediate-resistant *Staphylococcus aureus* (VISA) (Non Patent Literature 1), and VCM-resistant *Staphylococcus aureus* (VRSA) have been reported in recent years. Among these, a mechanism of resistance of VISA remains unknown. In addition, there has been an increase in the number of cases where the recurrence of infection is observed with a high frequency but its cause is unknown.

Under such situations, the present inventor and her colleagues extensively examined VCM-resistant bacteria, and as a result found slow-VISA, which is a resistant bacterium participating in the recurrence of infection, (Non Patent Literature 2), and revealed a mechanism of resistance and a mutated gene network due to exposure to antibacterial agents by analyzing SNPs, transcriptome, and metabolome of slow-VISA. Mutations found in slow-VISA were present in genes relating to stringent response or genes of the purine-pyrimidine synthetic pathway or the metabolic pathway of cell wall synthesis system. In particular, it was proved that mutations in rpoB (RNA polymerase) gene caused the resistance to multiple drugs such as a β-lactam drug (Non Patent Literature 3).

CITATION LIST

Non Patent Literature

Non Patent Literature 1: Lancet 350: 1670-1673
Non Patent Literature 2: Antimicrob. Agents Chemother. 58(9): 5024-5035
Non Patent Literature 3: Antimicrob. Agents Chemother. 57(10): 4861-4871

SUMMARY OF THE INVENTION

Problems to be Solved by the Invention

However, slow-VISA, which closely participates in the recurrence of infection and bacteremia, has not yet been detected from clinical samples, and the development of a means for detecting slow-VISA has been desired.

Therefore, an object of the present invention is to provide a new means for detecting slow-VISA from clinical samples.

Means for Solving the Problems

The present inventor has examined a means for detecting slow-VISA, and as a result has found that a preculture solution in which a population mainly consists of slow-VISA is obtained by the two-step culture including culturing slow-VISA, which grows slowly, at a low temperature and then at a physiological high temperature, and that slow-VISA can be detected with short time operation by culturing the preculture solution on a mupirocin-containing medium and a mupirocin-free medium, measuring MICs of VCM, and measuring changes in the MICs. On the basis of these findings, the present invention has been accomplished.

That is, the present invention provides the following [1] to [3].

[1] A method for detecting slow-VISA, comprising subjecting a sample to the following steps (a) and (b), or the following steps (a), (b), and (c), and determining the sample detected in step (b), or steps (b) and (c) as slow-VISA;

(a) a step of inoculating the sample into a BHI liquid medium, followed by culture at 30±2° C. for 18±2 hours and then at 37±2° C. for 18±2 hours;

(b) a step of inoculating the culture solution obtained in step (a) on a mupirocin-containing BHI medium or a mupirocin-free BHI medium, followed by culture for 48±2 hours, measuring a MIC of VCM, and detecting the sample having a MIC of VCM in the case of using the mupirocin-containing medium greater than a MIC of VCM in the case of using the mupirocin-free medium and greater than 6 μg/mL; and (c) a step of inoculating the sample grown in step (a) into a BHI liquid medium, followed by culture at 37±2° C. for 48±2 hours, then culturing the sample on a mupirocin-free medium, measuring a MIC of VCM, and detecting the sample having a MIC of VCM lower than the MIC of VCM in the case of using the mupirocin-containing medium in step (b) and forming a colony.

[2] The method for detecting slow-VISA according to claim 1, further comprising, in step (b), culturing the mupirocin-free medium comprising the sample for another 72±2 hours, and confirming colony formation which is not observed after the culture for 48±2 hours.

[3] The method for detecting slow-VISA according to claim 1 or 2, wherein the measurement of the MIC of VCM is performed by reading a scale on a strip placed on the medium at a point where an inhibitory zone after culture intersects the strip.

Effects of the Invention

According to the detection method of the present invention, slow-VISA, which could not be conventionally detected from clinical samples, can be detected with short time operation in a reliable manner. Rapid diagnosis of slow-VISA enables the reduction in unnecessary use of antibacterial agents, better chemotherapy with antibacterial agents, and the prevention and prediction of appearance of resistant bacteria, and the control of the appearance of antibacterial agent-resistant bacteria can be achieved.

BRIEF DESCRIPTION OF THE DRAWINGS

FIG. 1 shows an increase in the growth rate of slow-VISA in a medium containing 16 μg/mL of VCM by adding 0.032 μg/mL of mupirocin. In the figure, MUP indicates mupirocin.

FIG. 2 shows the results of the ETEST® testing system (μg/mL) of VCM for slow-VISA using a BHI agar medium. The pictures on the left show the results of a mupirocin-free medium after 96 hours, the pictures on the right show the results of a mupirocin-containing medium after 96 hours, and black arrows show the points after 48 hours.

FIG. 3 shows the results of a disk diffusion method of VCM for slow-VISA using a BHI agar medium. The disk diffusion method using 30 μg/mL vancomycin disks was separately performed on BHI agar media containing 0.032 μg/mL of mupirocin or BHI agar media in the absence of a drug. Small numerous colonies were detected as to slow-VISA after culture for 48 hours only around an inhibitory zone on a BHI agar medium containing 0.032 μg/mL of mupirocin. The values shown above the panels indicate the averages and standard deviations of the diameters of inhibitory zones.

MODES FOR CARRYING OUT THE INVENTION

The method for detecting slow-VISA of the present invention comprises subjecting a sample to the following steps (a) and (b), or the following steps (a), (b), and (c), and determining the sample detected in step (b), or steps (b) and (c) as slow-VISA;

(a) a step of inoculating the sample into a BHI liquid medium, followed by culture at 30±2° C. for 18±2 hours and then at 37±2° C. for 18±2 hours;

(b) a step of inoculating the culture solution obtained in step (a) on a mupirocin-containing BHI medium or a mupirocin-free BHI medium, followed by culture for 48±2 hours, measuring a MIC of VCM, and detecting the sample having a MIC of VCM in the case of using the mupirocin-containing medium greater than a MIC of VCM in the case of using the mupirocin-free medium and greater than 6 μg/mL; and (c) a step of inoculating the sample grown in step (a) into a BHI liquid medium, followed by culture at 37±2° C. for 48±2 hours, then culturing the sample on a mupirocin-free medium, measuring a MIC of VCM, and detecting the sample having a MIC of VCM lower than the MIC of VCM in the case of using the mupirocin-containing medium in step (b) and forming a colony.

The sample used in the present invention is, for example, urine, blood, expectoration, abscess, nasal mucosa, or the like, derived from a patient with infection. It is preferably a clinical sample from a MRSA carrier or a clinical sample which is suspected of containing bacteria causing MRSA infection and then is found to be infected with MRSA. It is particularly preferably a sample derived from a patient with infection who did not respond to VCM.

The medium used for step (a) may be a BHI (brain heart infusion) liquid medium, and a commercial BHI liquid medium can be used. Step (a) comprises culturing a sample at 30±2° C. for 18±2 hours and then at 37±2° C. for 18±2 hours. Even when cultured at 37±2° C. for 18±2 hours, slow-VISA did not grow sufficiently since it has a low growth rate. It is not until culture at 30±2° C. for 18±2 hours is first performed and further culture at 37±2° C. for 18±2 hours is then performed that a preculture solution in which a population consists mainly of slow-VISA is obtained. The amount of a sample inoculated into a BHI liquid medium is preferably $1 \times 10^5$ cells to $1 \times 10^6$ cells.

In step (b), the culture solution of step (a) is inoculated on a mupirocin-containing BHI medium or a mupirocin-free BHI medium, and is cultured for 48±2 hours. Then, the MIC (minimum inhibitory concentration) of VCM is measured.

As to the composition of the BHI medium used in step (b), it is preferable to contain mupirocin at a concentration at which the growth of bacteria is not suppressed in a usual BHI medium and to have a thickness of 4 mm±0.5 mm according to the Clinical & Laboratory Standards Institute (CLSI). More specifically, it is preferable to contain 0.005 μg/mL to 0.03 μg/mL of mupirocin in the BHI medium. A BHI agar medium is preferable as the BHI medium.

The content of mupirocin in the BHI medium is preferably 0.005 to 0.1 μg/mL which is a concentration at which the growth of bacteria is not prevented, and more preferably 0.005 to 0.03 μg/mL. The culture solution of step (a) is preferably inoculated on the BHI medium at about $1 \times 10^6$ cells to $1 \times 10^7$ cells. Culture is performed at 37±2° C. for 48±2 hours.

Although the measurement of the MIC of VCM may be performed by a method according to a usual broth dilution method or a usual agar dilution method, it is preferably performed by reading a scale on a strip placed on the medium at a point where an inhibitory zone after culture intersects the strip since heterogeneous groups can be determined. This MIC measuring means is widely adopted as the ETEST® testing method, and commercial ETEST® testing methods can be used. Alternatively, a disk diffusion method can also be used for the measurement of the MIC of VCM. In addition to the MIC of VCM, the MIC of cefoxitin may also be measured.

Detected is a sample having a MIC of VCM in the case of using the mupirocin-containing medium greater than a MIC of VCM in the case of using the mupirocin-free medium and greater than 6 μg/mL. It can be determined that this sample is suspected to be slow-VISA. When the MIC of cefoxitin is measured, a sample having a MIC of cefoxitin of 8 μg/mL or more (concentration used for the definition of MRSA by CLSI) is detected.

Further, when the mupirocin-free medium is cultured for another 72±2 hours and colony formation which is not found after the culture for 48±2 hours is confirmed, it can be confirmed that this sample is slow-VISA. Since the growth of slow-VISA is slow, it can be confirmed by this technique that this sample is slow-VISA.

In step (c), the sample grown in step (a) is inoculated again into a new BHI liquid medium, cultured at 37±2° C. for 48±2 hours, and then cultured in a mupirocin-free medium, and the MIC of VCM is measured.

It is preferable to inoculate $1 \times 10^5$ to $1 \times 10^6$ cells out of the BHI liquid medium grown in step (a) into the BHI liquid medium used in step (c). It is considered that slow-VISA grows by being cultured at 37±2° C. for 48±2 hours. Then, culture on the mupirocin-free BHI medium is performed, followed by the measurement of the MIC of VCM. The measurement of MIC is preferably performed by reading a scale on a strip placed on the medium at a point where an inhibitory zone after culture intersects the strip in the same way as step (b). The culture conditions for the MIC measurement are preferably at 37±2° C. for 48±2 hours. This medium for the MIC measurement is also preferably a BHI agar medium.

In step (c), it is determined that a sample having a MIC of VCM lower than the MIC of VCM in the case of using the mupirocin-containing medium in step (b) and forming a colony is slow-VISA.

In the method of the present invention, it can be determined that the sample detected in step (b) alone or steps (b) and (c) is slow-VISA. It is preferable to determine that the sample detected in steps (b) and (c) is slow-VISA.

According to the present invention, a preculture solution in which a population consists mainly of slow-VISA can be obtained in a short time by adopting step (a), and slow-VISA can be detected selectively by measuring the MIC of VCM by the culture using the mupirocin-containing BHI medium in step (b).

EXAMPLES

Next, the present invention will be described in more detail by way of Examples.

Example 1

(1) A single colony was inoculated into 4 mL of a BHI liquid medium of Eiken Chemical Co., Ltd., followed by stationary culture at 30±2° C. for 18±2 hours, and then shaking culture at 37±2° C. for 18±2 hours. Here, the used single colony is a strain selectively separated on a commercial MRSA selection medium by culturing blood derived from a patient with bacteremia who did not respond to treatment with VCM.

According to an existing method, preculture was performed at 37° C. overnight using a BHI liquid medium before the degrees of resistance to drugs (here, VCM which identifies VISA and cefoxitin, a beta-lactam drug, which identifies MRSA) were measured by the ETEST® testing system. In this method, since the growth of slow-VISA was slow, bacteria did not grow sufficiently.

Alternatively, preculture was performed at 37° C. for 2 days, but the population did not consist mainly of slow-VISA, only bacteria with decreased degree of resistance to VCM and rapid growth increased, and the original degree of drug resistance was not observed.

(2) The bacteria grown in step (a) is adjusted to OD=0.3 using an absorbance measuring instrument (wavelength of 578 nm), and it was set as 1×108 cells. Then, the bacteria are spread on a BHI agar medium of Eiken Chemical Co., Ltd. and a mupirocin-containing BHI agar medium, and the ETEST® strips (bioMerieux Japan Ltd.) of VCM and cefoxitin are placed thereon, followed by culture for 48 hours in accordance with the CLSI guideline. After 48 hours, tested bacteria having a MIC of cefoxitin of ≥8 µg/mL and a MIC of VCM of >6 µg/mL are suspected to be slow-VISA.

The present inventor found that mutations in nucleic acid metabolism-related genes often participated in the mechanism of resistance of slow-VISA. Further, it was supposed that the resistance further increased when the stringent response relating to those mutated genes was induced. Then, when the ETEST® testing method was performed on a BHI medium added with mupirocin, which induces the stringent response, at a concentration at which the growth was not suppressed, the degree of resistance increased, but the degree of resistance of a vancomycin-sensitive strain did not increase (FIG. 1 and FIG. 2).

FIG. 1(a) shows an increase in the growth rate of slow-VISA in a medium containing 16 µg/mL of VCM by adding 0.032 µg/mL of mupirocin. From FIG. 1(a), the growth rate in the case of culture in a liquid medium containing mupirocin at a concentration which did not prevent the growth of slow-VISA (in this case, 0.032 µg/mL) and 16 µg/mL of VCM was larger than the growth rate in the case of culture in a mupirocin-free liquid medium or a liquid medium containing mupirocin at a concentration which affected the growth and 8 µg/mL of VCM, and the difference in OD values therebetween was 1 or more in 24 hours. From FIG. 1(b), when VISA was used, an increase in the growth rate by the addition of mupirocin was not observed.

FIG. 2 shows the results of the ETEST® testing system (µg/mL) of VCM using an agar medium on which slow-VISA was spread. In addition, FIG. 3 shows the results of the disk diffusion method of VCM using the slow-VISA agar medium.

(3) The sample grown in step (a) was further inoculated into 4 mL of a new BHI liquid culture solution, followed by shaking culture at 37±2° C. for 48±2 hours and then culture in a mupirocin-free medium, and the MIC of VCM was measured in the same way as step (b). When the sample showed a MIC of ≤3 µg/mL and formed a colony after culture for 24 hours to 48 hours, the bacteria can be identified as slow-VISA.

The invention claimed is:

1. A method for detecting slow-vancomycin intermediate-resistant *Staphylococcus aureus*, the method comprising:
    (a) inoculating a sample into a brain heart infusion liquid medium by culturing at 30±2° C. for 18±2 hours and then at 37±2° C. for 18±2 hours;
    (b) inoculating the culture solution obtained in the inoculating (a) on a mupirocin-containing brain heart infusion medium and a mupirocin-free brain heart infusion medium by culturing for 48±2 hours, measuring a minimum inhibitory concentration of vancomycin, and detecting the sample having a minimum inhibitory concentration of vancomycin in the case of using the mupirocin-containing medium greater than a minimum inhibitory concentration of vancomycin in the case of using the mupirocin-free medium and greater than 6 µg/mL; and
    optionally, (c) inoculating the sample grown in the inoculating (a) into a brain heart infusion liquid medium by culturing at 37±2° C. for 48±2 hours, then culturing the sample on a mupirocin-free medium, measuring a minimum inhibitory concentration of vancomycin, and detecting the sample having a minimum inhibitory concentration of vancomycin lower than the minimum inhibitory concentration of vancomycin in the case of using the mupirocin-containing medium in the inoculating (b) and forming a colony and
    determining the sample detected in the inoculating (b), or the inoculating (b) and (c) as slow-vancomycin intermediate-resistant *Staphylococcus aureus*.

2. The method of claim 1, further comprising, in the inoculating (b):
    culturing the mupirocin-free medium comprising the sample for another 72±2 hours, and confirming colony formation which is not observed after the culture for 48±2 hours.

3. The method of claim 2, wherein the measuring of the minimum inhibitory concentration of vancomycin comprises reading a scale on a strip placed on the medium at a point where an inhibitory zone after culture intersects the strip.

4. The method of claim 1, wherein the measuring of the minimum inhibitory concentration of vancomycin comprises reading a scale on a strip placed on the medium at a point where an inhibitory zone after culture intersects the strip.

5. The method of claim 1, further comprising, prior to the inoculating (a):
    obtaining the sample from a methicillin-resistant *Staphylococcus aureus* carrier,
    wherein the sample comprises urine, blood, expectoration, abscess, or nasal mucosa.

6. The method of claim 1, further comprising, prior to the inoculating (a):
    obtaining the sample comprising urine from a patient.

7. The method of claim 6, wherein the patient has an infection and does not respond to vancomycin.

8. The method of claim 1, further comprising, prior to the inoculating (a):
    obtaining the sample comprising blood from a patient.

9. The method of claim 8, wherein the patient has an infection and does not respond to vancomycin.

10. The method of claim 1, further comprising, prior to the inoculating (a):
obtaining the sample comprising expectoration from a patient.

11. The method of claim 10, wherein the patient has an infection and does not respond to vancomycin.

12. The method of claim 1, further comprising, prior to the inoculating (a):
obtaining the sample comprising an abscess from a patient.

13. The method of claim 12, wherein the patient has an infection and does not respond to vancomycin.

14. The method of claim 1, further comprising, prior to the inoculating (a):
obtaining the sample comprising mucosa from a patient.

15. The method of claim 14, wherein the patient has an infection and does not respond to vancomycin.

16. The method of claim 1, further comprising, prior to the inoculating (a):
obtaining the sample comprising nasal mucosa from a patient.

17. The method of claim 1, wherein an amount of the sample inoculated in the inoculating (a) comprises $1\times10^5$ to $1\times10^6$ cells.

18. The method of claim 1, wherein an amount of the culture solution inoculated in the inoculating (b) comprises $1\times10^6$ to $1\times10^7$ cells.

19. The method of claim 1, wherein the mupirocin is present in the inoculating (b) in a concentration in a range of from 0.005 to 0.03 μg/mL of mupirocin in the brain heart infusion medium.

* * * * *